United States Patent [19]

Copney

[11] Patent Number: 4,752,476
[45] Date of Patent: Jun. 21, 1988

[54] SLEEP AIDING HERBAL COMPOSITION AND METHOD OF UTILIZING SAME

[76] Inventor: Claudette V. Copney, 5129 S. University, Chicago, Ill. 60615

[21] Appl. No.: 831,132

[22] Filed: Feb. 18, 1986

[51] Int. Cl.[4] ............................................. A61K 35/78
[52] U.S. Cl. ................................. 424/195.1; 514/923
[58] Field of Search ...................... 424/195.1; 514/923

[56] References Cited

U.S. PATENT DOCUMENTS 4,671,956  6/1987  Warren et al. ................... 424/195.1

OTHER PUBLICATIONS

M. Keller, "Mysterious Herbs & Roots", pp. 250–251, 1978.
D. Law, "The Concise Herbal Encyclopedia", pp. 241–242, 1973.
Steinmetz, Codex Vegetabili, 1957, No. 726, 740, 738, 635 and 836.

*Primary Examiner*—John Rollins
*Attorney, Agent, or Firm*—Laff, Whitesel, Conte & Saret

[57] ABSTRACT

A composition to be ingested after boiling by an individual for the purpose of inducing sleep in the individual comprising ingredients mixed in the following ratios: seven ounces of water, one and one-half tablespoons of rose water, two teaspoons of nutmeg, nine bay leaves, and two and one-half tablespoons of spearmint.

14 Claims, No Drawings

SLEEP AIDING HERBAL COMPOSITION AND METHOD OF UTILIZING SAME

The present invention relates to a novel composition which has been found to induce sleep among those individuals who have difficulty falling asleep when they desire to do so. The invention also relates to a method of using my novel composition to induce sleep.

BACKGROUND OF THE INVENTION

Many individuals, both adult and children, find it difficult to fall asleep upon retiring at the end of the day. This can be caused by many factors, such as stress resulting from the day's activities, anxiety about future problems, or physical impediments to falling asleep. If a person cannot fall asleep when desired, and obtain his or her minimum requirement of rest, that person finds it difficult to function at an optimum level the next day, causing shortcomings in his or her work, business, or school efforts. Therefore, there is a need to develop aids for individuals who have difficulty in falling asleep naturally and restfully at the end of the day.

The present invention provides such an aid to persons desiring to fall asleep naturally, without the ingestion of harmful or debilitating drugs. It has been discovered that the composition of the present invention, when prepared properly and administered to an individual will induce natural, restful sleep in that individual shortly after ingestion by normal swallowing.

Therefore, it is a primary object of the present invention to provide a novel composition, and method of preparing such composition, which will induce natural and restful sleep in an individual who heretofore encountered difficulty falling asleep at night.

Another object of the present invention is to provide a method of treating and administering to an individual for the purpose of inducing natural and restful sleep in that individual.

An additional object of the present invention is to provide a sleep inducing composition which, when used by an individual, is not habit forming, and which has been discovered to be suitable for use with satisfactory results at those times when an individual feels the need for a sleep-inducing compound.

These and other objects of the present invention are provided by the composition and method of using same as described hereinbelow.

My composition has been effectively utilized to induce sleep in humans. The composition comprises a mixture of rose water, nutmeg, bay extract and spearmint. The composition comprises the following: the nutmeg belongs to the family myristicaceae and the genus myristica; the bay extract belongs to the family lauraceae, the genus laurus, and the species nobilis (bay leaves); and the spearmint belongs to the family labiatae and the genus mentha. These ingredients when combined provide an effect which is not provided by the individual ingredients per se.

To provide for the ease of ingesting this composition, my mixture is added to water and the water is boiled for 15 to 30 minutes, preferably 15 to 20 minutes, to produce a drinkable solution. Of course, if a concentrated solution is desired, the water is boiled for a longer period of time and the concentrated solution can then be used at a later date in a diluted form.

Although I have not prepared my mixture as a tablet or in a powder form, I assume that this could be done by a knowledgeable chemist.

My preferred composition for inducing sleep in an adult is prepared as follows for a single dosage, one and one-half (1½) tablespoons of rose water is added to seven (7) ounces of water. This is usually mixed in a cooking vessel such as a tea pot. To this mixture is added two (2) teaspoons of nutmeg, nine (9) bay leaves, the two and one-half (2½) tablespoons of spearmint.

The composition is then heated and gently boiled for from fifteen to twenty minutes. The tea pot is then removed from the heat, and the composition is allowed to cool to drinking temperature—the temperature of what one would normally drink a glass of warm water.

The bay leaves are removed from the pot or allowed to remain behind as solution is poured into a drinking glass. The solution is usually drunk by the adult ten (10) to twenty (20) minutes prior to going to bed.

The amount of liquid left is less than the eight and one-half (8½) ounces that was started with. Usually, there is between 5 and 7½ ounces of liquid. The individual can consume the full five to seven and one-half ounces of the composition, or may drink as much as he or she feels may be needed to induce sleep. I have found that at least one-half of the contents should be drunk to produce the described results.

It has also been discovered that the above-described composition acts as a mild diuretic. This result is believed to be provided by the spearmint which forms part of the composition.

Although I describe my preferred embodiment by mixing all of the ingredients at once, the same effect can be produced by mixing them in any order and at different time intervals. For instance, any composition can be prepared by placing the bay leaves in either their whole form or ground form into water and boiling the water. The resulting mixture is then filtered to remove any residue. The bay extract is then mixed with rose water, nutmeg and Spearmint to provide my sleep inducing composition.

The above description is made only by way of example and not as a limitation to the scope of my invention as set forth in the objects thereof and in the accompanying claims.

I claim:

1. A sleep inducing composition comprising a mixture of water, rose water, nutmeg, bay extract and spearmint, in the following proportions:
    Water: 7 ozs.
    Rose Water: 1½ tablespoons
    Nutmeg: 2 teaspoons
    Bay: Extract of 9 bay leaves boiled
    Spearmint: 2½ tablespoons.

2. The sleep inducing composition of claim 1 wherein said bay extract is prepared by boiling bay leaves in water and removing the bay leaves to provide the desired bay extract.

3. The composition of claim 2 wherein the ingredients are further boiled for 15 to 30 minutes.

4. The method of claim 1 wherein:
    the mixture of step (a) is boiled for a range of fifteen to twenty minutes.

5. The sleep inducing composition of claim 1 wherein said nutmeg is a member of the family myristicaceae and the genus myristica.

6. The sleep inducing composition of claim 1 wherein said bay extract is a member of the family lauraceae and the genus laurus.

7. The sleep inducing composition of claim 1 wherein said bay extract is a member of the species *nobilis*.

8. The sleep inducing composition of claim 1 wherein said spearmint is a member of the family labiatae and genus mentha.

9. A sleep inducing composition comprising a mixture of water, rose water, nutmeg, bay leaves and spearmint, in the following proportions:
Water: 7 ozs.
Rose Water: 1½ tablespoons
Nutmeg: 2 teaspoons
Bay Leaves: 9
Spearmint: 2½ tablespoons.

10. The method of preparing a composition to be ingested by an individual for the purpose of inducing sleep in said individual comprising the steps of:

(a) combining the following ingredients in the following ratios;
water: 7½ ounces
rose water: 1½ tablespoons
nutmeg: 2 teaspoons
bay leaves: 9
spearmint: 2½ tablespoons
(b) boiling the mixture of step (a) for 15 to 30 minutes.

11. The method of preparing a composition in claim 10 wherein said nutmeg is a member of the family myristicaceae and the genus myristica.

12. The method of preparing a composition in claim 10 wherein said bay extract is a member of the family lauraceae and the genus laurus.

13. The method of preparing a composition in claim 10 wherein said bay extract is a member of the species *nobilis*.

14. The method of preparing a composition in claim 10 wherein said spearmint is a member of the family labiatae and the genus mentha.

* * * * *